United States Patent
Jeckelmann et al.

(10) Patent No.: US 7,782,192 B2
(45) Date of Patent: Aug. 24, 2010

(54) ENERGY-OPTIMISED DATA TRANSMISSION FOR A MEDICAL APPLIANCE

(75) Inventors: Joel Jeckelmann, Villars-sur-Glane (CH); Michael Shoemaker, Mannheim (DE); Sybille Fankhauser, Zollikofen (CH); Sebastiaan La Bastide, Muri b. Bern (CH); Gunnar Meyer Olden, Burgdorf (CH); Matthias Essenpreis, Burgdorf (CH); Nicole Bernini, Ersigen (CH)

(73) Assignee: Roche Diagnostics International AG, Steinhausen (CH)

( * ) Notice: Subject to any disclaimer, the term of this patent is extended or adjusted under 35 U.S.C. 154(b) by 0 days.

(21) Appl. No.: 11/924,236

(22) Filed: Oct. 25, 2007

(65) Prior Publication Data

US 2008/0129486 A1 Jun. 5, 2008

Related U.S. Application Data

(63) Continuation of application No. PCT/EP2006/003869, filed on Apr. 26, 2006.

(30) Foreign Application Priority Data

Apr. 26, 2005 (DE) ........................ 10 2005 019 306

(51) Int. Cl.
*G08B 1/08* (2006.01)
(52) U.S. Cl. .............................. 340/539.12; 340/539.3; 607/1

(58) Field of Classification Search ............ 340/539.12; 607/1
See application file for complete search history.

(56) References Cited

U.S. PATENT DOCUMENTS

| 4,396,295 | A | 8/1983 | Ishikawa |
| 5,113,869 | A * | 5/1992 | Nappholz et al. ............ 600/508 |
| 6,239,724 | B1 | 5/2001 | Doron et al. |
| 6,551,276 | B1 | 4/2003 | Mann et al. |
| 2002/0072784 | A1 | 6/2002 | Sheppard, Jr. et al. |
| 2004/0199212 | A1* | 10/2004 | Fischell et al. ................ 607/32 |
| 2004/0204744 | A1 | 10/2004 | Penner et al. |
| 2005/0065464 | A1 | 3/2005 | Talbot et al. |
| 2007/0208235 | A1 | 9/2007 | Besson et al. |

FOREIGN PATENT DOCUMENTS

| DE | 92 15 558.8 U1 | 2/1993 |
| DE | 43 29 898 A1 | 6/1995 |
| EP | 1 343 112 | 9/2003 |

* cited by examiner

*Primary Examiner*—Jeffery Hofsass
(74) *Attorney, Agent, or Firm*—Dorsey & Whitney LLP

(57) ABSTRACT

A medical appliance for use on and/or in the body of a user including a transmission unit and an activation switch connected to the transmission unit for activating the transmission unit when an activation signal is received by the activation switch. The invention encompasses systems and processes for transmitting data between a medical appliance and an external appliance, wherein, in some embodiments, the external appliance activates the medical appliance prior to data transmission when the latter is in an idle state.

11 Claims, 5 Drawing Sheets

ENERGY-OPTIMISED DATA TRANSMISSION FOR A MEDICAL APPLIANCE

CROSS REFERENCE TO RELATED APPLICATION(S)

This application is a Continuation of International Patent Application PCT/EP2006/003869, filed on Apr. 26, 2006, which claims priority to German Application No. 10 2005 019 306.4, filed on Apr. 26, 2005, the entire contents of both of which are hereby incorporated by reference.

BACKGROUND

The present invention relates to devices for injecting, infusing, delivering, administering or dispensing substances, and to methods of making and using such devices. More particularly, it relates to a medical appliance or device, a system comprising a medical device or devices and data transmission, and a method of operating an energy-optimised data transmission from and/or to a medical appliance.

When a medical appliance (the term medical device may be used synonymously herein) is being operated, for example an infusion pump or a sensor attached to the skin of a user, it is advantageous for a user if data for operating the medical appliance can be transmitted to the medical appliance from a remote control, for example, or if sensor measurement data can be transmitted to an external device.

U.S. Pat. No. 6,551,276 discloses an external infusion device which can be activated by a remote control. The infusion device has a receiver which may be in a so-called standby mode and can be automatically activated approximately every 2.5 seconds to ascertain whether a radio signal was emitted by the remote control, as a result of which the radio remote control is designed to emit an activation signal over a period of approximately 5 seconds, for example, so that it can be detected by the receiver.

U.S. Pat. Nos. 6,551,276 and 4,396,295 describes an implantable measuring appliance, which has a unit for dispensing a dose. An external control device can be coupled with this appliance to vary the infusion rate, for example.

SUMMARY

It is an object of the present invention to provide a medical appliance, a system and a method which utilize and/or permit data transmission using a low amount of energy.

In one embodiment, the present invention comprises a medical system comprising a medical device comprising a communication unit and an activation element connected to the communication unit wherein the activation element activates the communication unit, and a remote control comprising a data input unit, an activation unit for activating the activation element of the medical appliance and a communication unit able to communicate with the communication unit of the medical appliance.

In one embodiment, the present invention comprises a medical appliance, such as a subcutaneous sensor, a glucose sensor, a pump, an insulin pump, etc., which can be implanted and may be minimally invasive or non-invasive, or an injection pen for use on and/or in the body of a user. The appliance has at least one electric or electronic functional unit, such as a measuring sensor, a processor, a memory or an electric motor, which can be activated by the processor, and a transmitter and/or receiver unit for transmitting, sending and/or receiving or communicating data. In some embodiments, the invention comprises an activation switch connected to the transmitter and/or receiver unit and/or to the at least one electronic functional unit. In some embodiments, the activation switch can be activated by an external activation signal to activate the transmitter and/or receiver unit and/or the at least one electronic functional unit so that a wireless communication link can be established to transmit data, e.g., measurement information, from a sensor to an external device to control data for setting a base rate, to dispense a bolus to an insulin pump, or to synchronise appliances connected by the communication link(s).

In one embodiment, the present invention comprises a method of using a medical system comprising the steps of providing a medical device comprising a communication unit and an activation element connected to the communication unit wherein the activation element activates the communication unit, providing a remote control comprising a data input unit, an activation unit for activating the activation element of the medical appliance and a communication unit able to communicate with the communication unit of the medical appliance, and placing the medical device and remote control in proximity sufficient for the communication units to communicate with each other. Further, in some embodiments, when the communication units are not in communication, the medical device is in an idle state and may be activated by the remote control prior to the communication.

In some embodiments, for the purpose of the present invention, the communication takes place as and when required only, in other words on demand. Thus, the activation switch needed for activating the data transmission is such that it ensures that a communication can be set up or established only when the receiver and transmitter, in other words, the medical appliance and an external device, such as a control device or its respective input/output units, are either in direct physical contact with one another or are disposed relative to one another so that there is a drop below a predefined maximum distance between the transmitter and receiver. In some embodiments, the activation switch of the medical appliance, which can be activated by an activation element of the external device, can not issue an activation or authorisation signal unless the medical appliance and an external device assume a predefined orientation with respect to one another, in other words the transmitter and receiver units or transmitter and receiver elements are relatively adjacent and/or opposite one another.

This enables the energy requirement of the medical appliance to be reduced because electric or electronic components for transmitting data are not activated unless a co-operating transmitter or receiver of an external device is within range. The transmitter and receiver units may be dimensioned or designed so that a data transmission has to be operated over a relatively short distance only, such as 5 cm or less, for example, which is sufficient for data to be transmitted from an external device attached to the clothing of a user, for example, through this clothing to the skin of a patient disposed underneath or an implanted medical appliance, or received by this medical appliance. Since a data transmission unit in accordance with the present invention is required to have only a relatively low power capacity, it may be of a relatively small design compared with data transmission units designed to operate at distances in the range of a meter or so, and the transmitter and receiver elements, such as antenna, induction coils or other elements transmitting or receiving electromagnetic waves, such as lamps, photo-diodes, loudspeakers, microphones, etc., need only a short range and power capacity.

In some embodiments, the activation switch may also be an element or component by which power supplied by the external device can be received or picked up to communicate with the external device or to perform an action predefined by the external device. Thus, the medical appliance does not require a power supply because requisite energy is supplied by the external device. The activation switch may be provided in the form of an induction coil, for example, and an external device disposed in the vicinity of the induction coil may also have an induction coil and may transmit power to the medical appliance via the inductive coupling of the induction coils, so that the medical appliance and/or external device are activated and able to take and/or receive a measurement or control information, for example.

Alternatively or in addition, in some embodiments, an activation switch in the form of a magnetic switch may also be provided, for example in the form of a reed contact, which is activated by an external magnetic field, in other words a permanent magnet or electro-magnet provided on the external device. In this case, a link may be established with the electric or electronic components provided in the medical appliance, such as the transmitter and receiver unit, with a power source likewise provided in the medical appliance in the form of a battery or accumulator. Other sensors which are able to detect electromagnetic fields, sound or light, or magnetic or capacitive effects may also be used as activation switches, e.g., a photo-diode, a microphone, etc.

In this respect, the activation switch may be designed so that a communication link established by an external device after activation is cut off again if an activation signal is no longer being received. In other words, if a predefined minimum distance from the external device is exceeded or exceeded again. Alternatively or in addition, the medical appliance may be activated for only a predefined period needed to transmit data or for running a predefined action, such as dispensing a bolus and/or transmitting an operating signal.

In some embodiments, the activation switch may be provided in the form of a mechanical switch, for example underneath a rubber-type surface element, which activates the power supply or a transmitter/receiver unit of the medical appliance when a mechanical switching operation is initiated, for example when a pressure is applied to the mechanical switch by an external device attached to the medical appliance. This being the case, the medical appliance may have a surface profile which co-operates with a complementary profile of the external device so that the external device has to be attached to the medical appliance by the surface profile in a specific orientation to activate it or to establish a data link. In the case of a direct contact between the medical appliance and the external device, a data link or alternatively a power transmission may also take place via an electric wire when co-operating contact elements of the medical appliance and external device are in contact with one another.

The present invention further relates to a control device, such as a remote control or a blood glucose measuring device for activating a medical appliance of the type outlined above. In some embodiments, the control device has an external device in the form of an activation unit, by which one or more activation switches of the medical appliance can be activated or operated. The activation unit on the external device may be a magnet, for example, e.g., a permanent magnet or an electromagnet, an induction coil for transmitting power to the medical appliance, a loudspeaker, a lamp or a specific surface profile for operating a mechanical switch. The control device also has a transmitter and/or receiver unit which is able to establish a data link with the medical appliance, in which case the transmitter and/or receiver unit is activated when the activation unit of the control device emits an activation signal or the control device detects that a connection with the medical appliance has been established or exists, such as a mechanical contact, a radio link and/or an inductive coupling.

In some embodiments, the external device may have an input unit, for example a keyboard or a touch screen, to enable a user to enter control signals in the control device which can be transmitted by it to the medical appliance to control the operating mode of an implanted insulin pump, for example, such as setting the base rate or a bolus. In some preferred embodiments, the control device has a display unit or a display, on which control data to be transmitted, commands or parameters entered by a user or data received from the medical appliance, such as measurement data of a sensor, can be displayed.

In some preferred embodiments, the control device has an interface for communicating with another electric device, such as a USB interface, an infrared interface or a Bluetooth interface, for example, to enable data to be exchanged with a computer, a mobile telephone or a PDA, for example, in other words to enable what might be termed a "long-range" communication to be run.

The present invention further relates to a system of transmitting data with a medical appliance of the type described above which can be carried on or in the body of a patient and an external control device of the type described above, wherein the devices can be synchronised once the transmitter and/or receiver unit has been activated.

By virtue of another aspect of the present invention, it also relates to a method of transmitting data between a medical appliance and an external device, wherein, when the medical appliance is in the idle state, it can be activated by the external device prior to the data transmission. This being the case, the medical appliance may remain in an idle state consuming only a small amount of energy or none at all if an external device is not provided or activated for establishing a data link, in which case the medical appliance consumes energy only for the data communication if it has been activated beforehand by an external or control device which is ready for the data transmission.

In some preferred embodiments, the medical appliance is activated without contact, for example by an electric, magnetic or electromagnetic field, sound and/or light. It would also be possible to activate the medical appliance by a direct physical contact with the control device. In some preferred embodiments, the medical appliance is only activated when there is a drop below a predefined distance of 2 to 10 cm, for example, in which case an activation switch of the medical appliance can cut off a communication between the latter and an external device again if the predefined distance is exceeded or exceeded again. In some embodiments, the medical appliance may also be activated on the basis of a specific time limit or may be terminated when the medical appliance has completed an action, such as transferring measurement data from the memory of a sensor via the transmitter and receiver units to the external device. Such measurement data can be deleted from the memory of the medical appliance once it has been transmitted to the external device or after a confirmation signal has been received acknowledging that the transmitted data has been correctly received. In the case of such a data transmission, all the data compiled since the last data exchange, for example measurement values with associated detection times, can be transmitted and deleted so that the memory of the medical appliance is available for storing new data only.

In some preferred embodiments, identification codes may be transmitted by the medical appliance and/or the external device to prevent data being inadvertently transmitted between other, unrelated systems. The identification code may be part of a radio protocol, for example, and may be permanently programmed in a system component. Another option would be for the identification code to be freely programmable when the system is started up, in which case two components can be coupled with one another when activated by a user. In some embodiments, RFID tags on the medical appliance may also be used in conjunction with RFID transponders on the control device for identification purposes.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to electrical systems and components of the invention. In embodiments with electrical features and/or components, suitable electrical components and circuitry, wires, wireless components, chips, boards, microprocessors, computers, inputs, outputs, displays, control components, etc. may be used. Generally, unless otherwise indicated, the materials for making the invention and/or its components may be selected from appropriate materials such as metal, metallic alloys, ceramics, plastics, etc.

Figure 1:
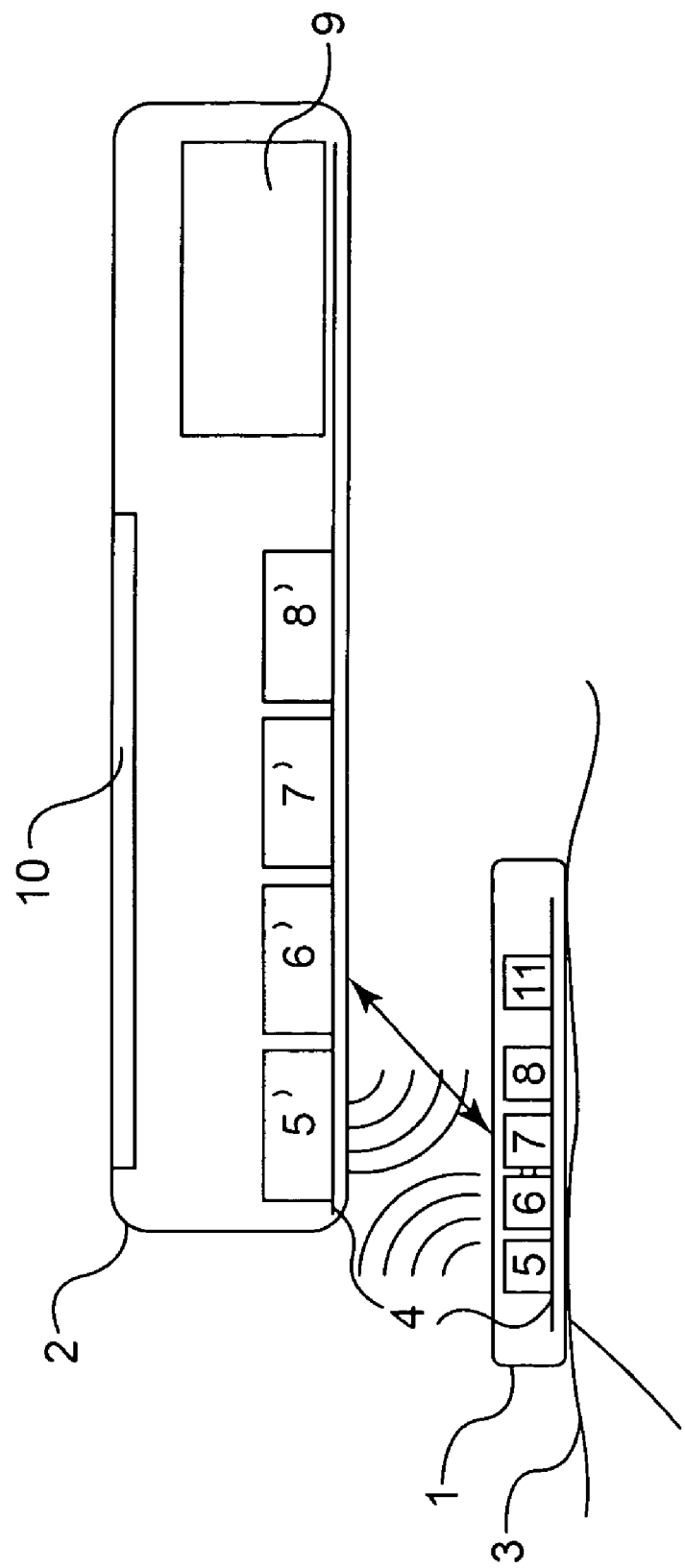
FIG. 1 illustrates one embodiment of the present invention comprising a system for activating a medical appliance by power transmitted from a control device.

FIG. 1 illustrates a first embodiment of a system in accordance with the present invention with a medical appliance 1 which can be worn on the skin 3 by a user undergoing out-patient treatment, which may be attached to the skin 3 or implanted, and which may be a pump or a sensor, for example. The medical appliance 1 has an induction coil 6 for picking up power transmitted via an inductive coupling from a co-operating induction coil 6' of an external control device 2, and the induction coil 6 of the medical appliance 1 acts as an activation switch for the transmitter/receiver unit 5 and the processor 7 of the appliance 1 and is supplied with power by the induction coil 6. The processor 7 is coupled with a memory 8 and is also able to activate the transmitter/receiver unit 5 once it has been activated, for example to transmit measurement or configuration data from the memory 8 via the unit 5 to the co-operating transmitter/receiver unit 5' of the external control device 2 or process data received in the opposite direction, for example configuration data for the medical appliance 1, and/or store it in the memory 8. A battery 11 may optionally also be provided in the medical appliance 1, which supplies the power needed for a sensor or pump function of the medical appliance 1, for example, thereby obviating the need for a power supply in the medical appliance 1 for the data communication.

Like the medical appliance 1, the external control device 2, which might be a blood glucose measuring device for example, also has a processor 7' and a memory 8' to enable data entered by a user via a touch screen 10 and/or received from the medical appliance 1 to be stored or for transmitting data to the medical appliance via the transmitter/receiver units 5, 5'. A battery or an accumulator 9 is also provided for supplying the external control device 2 with power. A communication can therefore be established between the medical appliance 1 and the external control device 2 once activated by means of the induction coils 6, 6' due to a transfer of power, and once the data transmission between these devices has terminated, the memory of the control device 2 may be read by another device, of a type that will be described with reference to FIGS. 3 and 4, for example.

The electronic component units 5-9 and 11 are mounted on a board 4 in the example illustrated.

Figure 2:
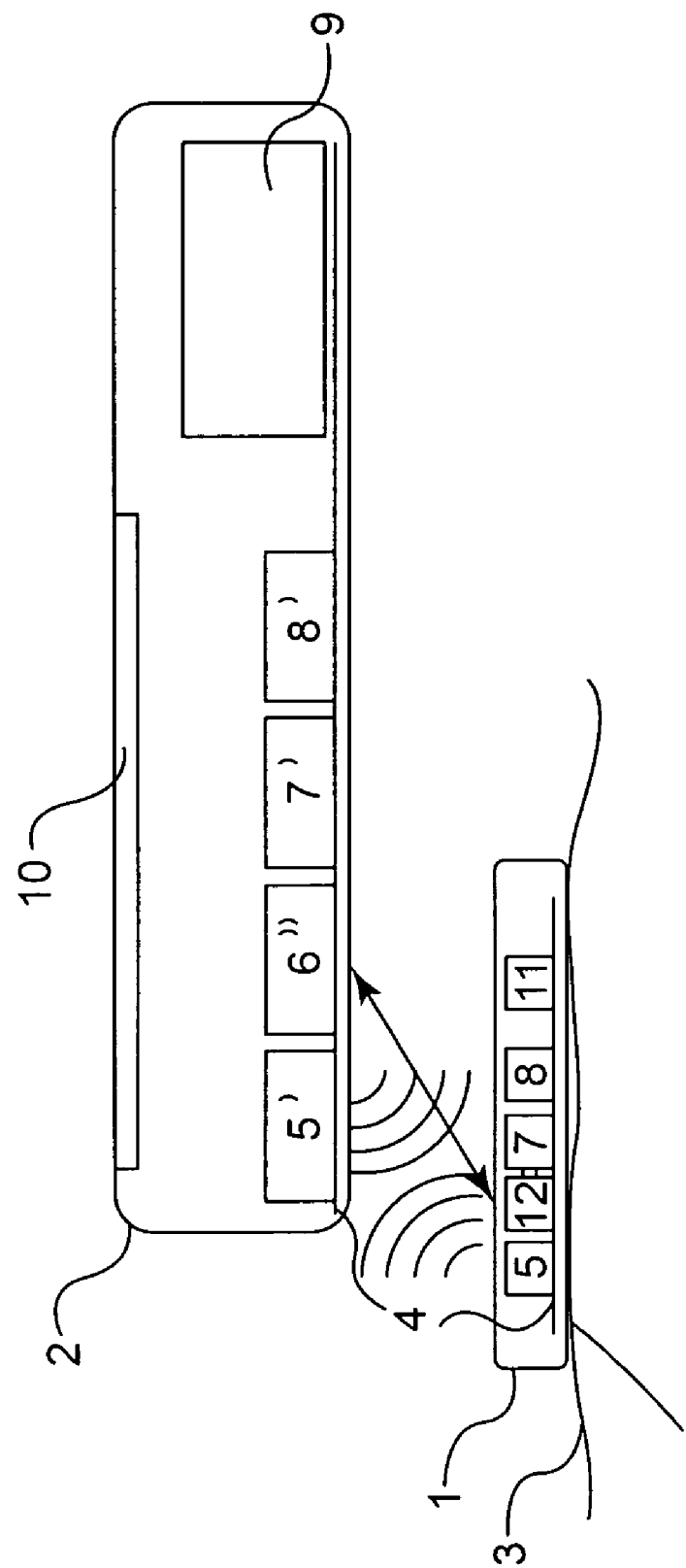
FIG. 2 illustrates a second embodiment of the present invention comprising a system for activating a medical appliance via a permanent magnet.

FIG. 2 illustrates a second embodiment of a system which differs from the first embodiment illustrated in FIG. 1 due to the fact that a permanent magnet 6' is provided in the control device 2 to activate a magnetic switch 12 in the medical appliance 1, such as a reed contact for example, so that the magnetic switch 12 serving as the activation switch is able to activate the transmitter/receiver unit 5 and/or the processor 7 of the medical appliance 1 and release it for a data transmission.

Figure 3:
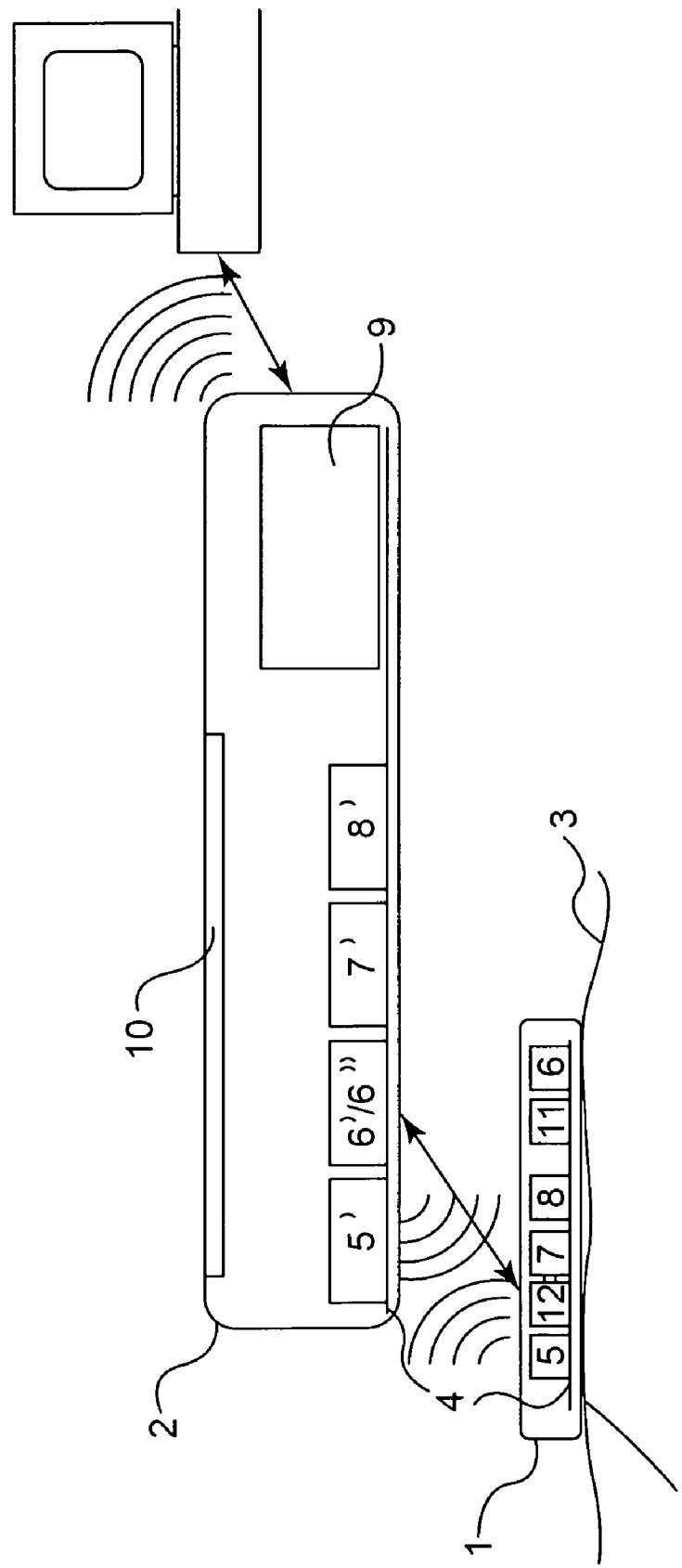
FIG. 3 illustrates a third embodiment of the present invention comprising a system with the capability for long-range communication.

FIG. 3 illustrates a third embodiment of the present invention comprising a system wherein a medical appliance 1 is activated or transmits data by the external control device 2, for example due to an induction coil 6' or a permanent magnet 6" which co-operates with an induction coil 6 or a magnetic switch 12 of the medical appliance 1. The external control device 2 is also designed so that a data link can be established with another external device 13, such as a PC, a mobile telephone, a PDA, or the like, for example, so that data transmitted to it from the medical appliance 1, for example, can be transmitted to the external unit 13 or received from it in the opposite direction.

Figure 4:
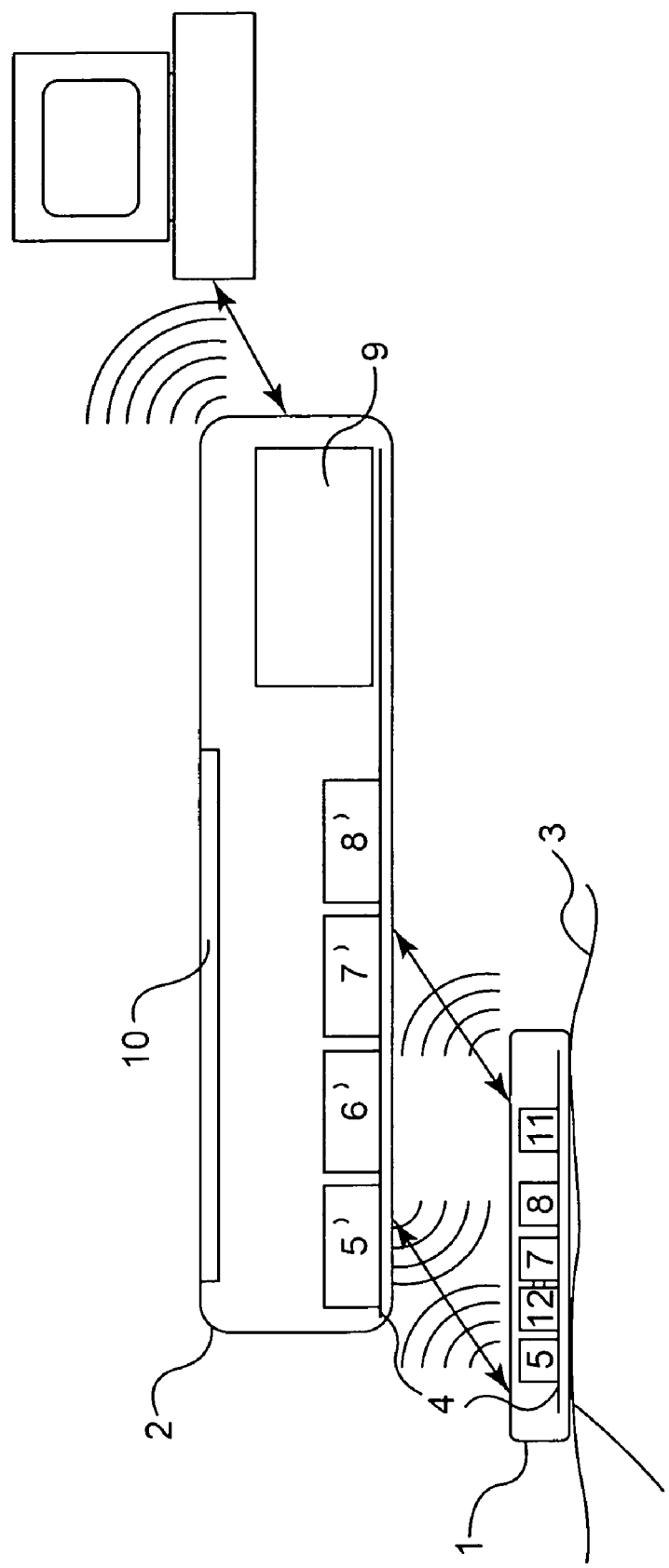
FIG. 4 illustrates another embodiment of the present invention comprising a system which permits the transmission of simple signals across larger distances.

FIG. 4 illustrates a fourth embodiment of the present invention which, like the third embodiment illustrated in FIG. 3, is also able to run a data communication across a greater distance between the medical appliance 1 and the control device 2 for specific signals, such as short status signals for example. To this end, the transmitter/receiver unit 5 of the medical appliance 1 may be designed so that a status or request signal is emitted briefly across several metres using a higher amount of energy, for example, which may also be transmitted across a greater distance to the control device 2 to signal to a user of the control device 2 that a communication must be established with the medical appliance 1.

Figure 6:
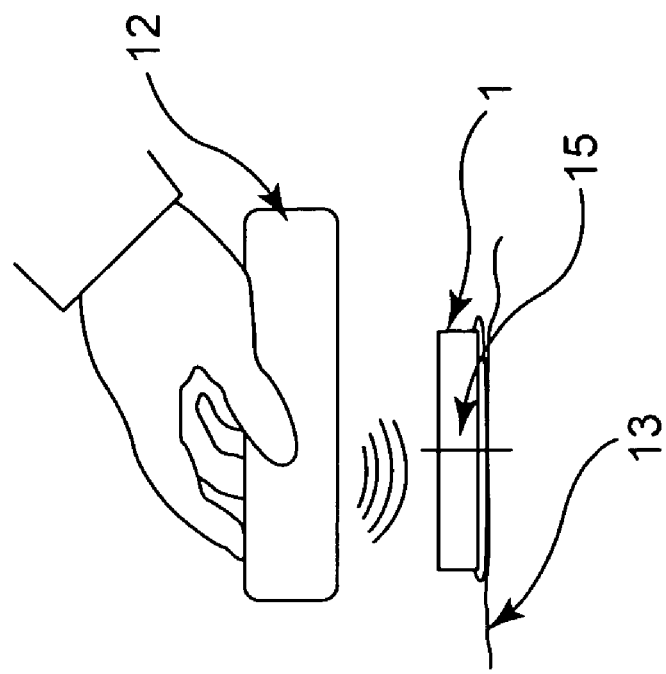
FIG. 6 shows the embodiment illustrated in FIG. 5 during the data exchange between an exemplary medical appliance and an exemplary control device.
Figure 5:
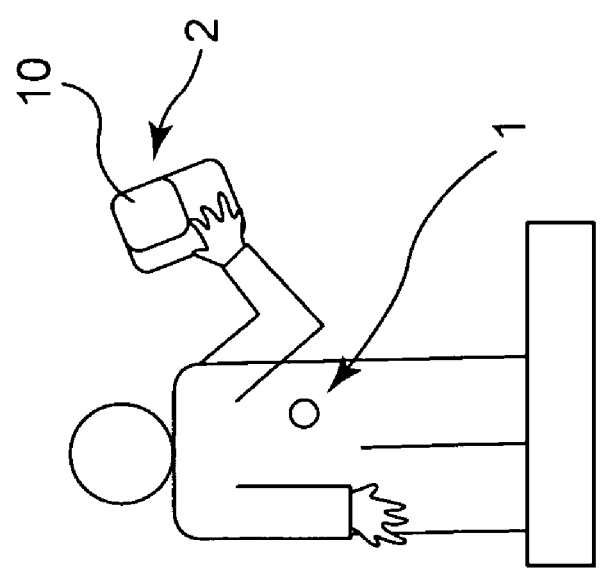
FIG. 5 illustrates another embodiment of the present invention, a system comprising a medical appliance and a control device which permits a data exchange between the appliance and the device.

FIGS. 5 and 6 illustrate a fifth exemplary embodiment of the present invention, namely a system which permits a data exchange between a medical appliance 1 which can be carried on the skin 3 of a user undergoing out-patient treatment, such as a sensor or a pump or infusion pump or a so-called patch module, and an external control device 2 which may be mobile or carried by a user, such as a blood sugar measuring device. The medical appliance 1, which may be attached to the skin 3 or implanted, has a needle 15 by which small samples of the user's blood can be taken. The medical appliance 1 may also be subcutaneous or disposed under the user's skin 3 or may take small quantities of the user's blood on a minimally invasive basis. The medical appliance 1 comprises a computer unit, such as a processor or micro-processor, a memory, a transmitter/receiver unit, a power source such as a battery and/or an induction coil of the type described above and/or a magnetic switch of the type described above, and a measuring unit, such as an electronic circuit for measuring or detecting at least one physiological parameter of the user, in particular the blood sugar value or blood glucose level from the sampled blood. The measuring unit may operate on an optical basis so that the blood sample reacts with different chemical substances causing a test field to change colour. This colour change may be detected by the measuring unit and the blood sugar value determined on the basis of the duration and intensity of the change. The measuring unit may also operate on an amperometric basis, in which case the blood sugar value can be determined from the blood by measuring the curve of a current intensity.

The external control device 2, which may be a blood glucose measuring device or data logger, has a display unit 10, in particular a screen or a display or a touch screen, a transmitter/receiver unit, a memory, a power source such as a battery, and at least one computer unit, e.g., a processor or micro-processor. The external control device 2 may also have an activation switch of the type described with reference to FIGS. 1 to 4, e.g., an induction coil or a permanent magnet. The control device 2 may be designed so that it can determine the blood sugar value or plot the blood sugar value of the user from measurement data and display it on the display unit 10 by outputting figures or showing a graph or diagram.

As illustrated in FIG. 6, the external control device 2, such as the blood sugar measuring device, may be fitted in the vicinity or range of the medical appliance 1, such as the patch module, to permit a data exchange or data transmission between the control device 2 and the medical appliance 1. To this end, the activation switch of the control device 2 preferably activates the activation switch of the medical appliance 1 to enable power to be transmitted from the activation switch of the control device 2 to the activation switch of the medical appliance 1, by which the medical appliance 1 can be supplied with current. The activation switch of the control device 2 may also activate the power source or power supply of the medical appliance 1 so that when the power source is activated, the medical appliance 1 can be supplied with current.

A blood value can be determined by the medical appliance 1 from a user's blood. This value may be transmitted by the transmitter/receiver unit of the medical appliance 1 to the transmitter/receiver unit of the control device 2 together with additional information, such as the time the blood sample was taken, for example, when the medical appliance 1 is disposed sufficiently close to the control device 2, thereby permitting a data transmission. In the control device 2, the computer unit of the control device 2 can determine the blood sugar value or glucose content from this blood and store it in the memory together with the additional information or display it on the display unit 10.

The blood sugar value or glucose level of the user can also be determined in the medical appliance by, the computer unit from the user's sampled blood and transmitted together with the additional information in the position or disposition on the control device 2 illustrated in FIG. 6, for example. At different points in time, recorded blood sugar values can be stored in the memory of the medical appliance 1 together with the time or instant of sampling and retrieved by the external device 2 as and when needed. Data pertaining to the detected blood sugar level and optionally the additional information may be transmitted by the transmitter/receiver unit of the medical appliance 1 to the transmitter/receiver unit of the control device 2 and stored in the memory of the control device 2 or shown on the display unit 10 of the control device 2 in the form of values or as a diagram. For example, several blood sugar values obtained at different times can be stored in the control device 2 and displayed graphically as a function of time if necessary to produce a diagram showing the blood sugar level of a user. Individual values in the blood sugar level diagram may be selected by the user by the touch screen, for example, or by another input unit, which can then be output as values. In particular, for example, directly after receiving the blood sugar value from the medical appliance, the blood sugar value can be output on the display unit 10 of the control device 2. The control device 2 may also be held in the activation range of the medical appliance 1 so that the transmitter/receiver unit of the control device 2 is able to send an activation signal to the medical appliance 1 for example, whereupon the medical appliance 1 is activated and takes a blood sugar measurement and/or transmit a detected blood sugar value to the control device 2, which can then be output on the display unit 10 of the control device 2.

The detected data pertaining to the user's glucose level or the glucose level curve may be transmitted via an interface provided on the control device 2, such as an infrared or Bluetooth or FireWire interface, to an external computer unit, such as a computer, and processed in the computer unit or output or displayed and/or evaluated by display or evaluation software.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A medical system comprising:
   a) a medical device for use on or in a user's body, comprising a transmitter/receiver unit and an activation switch connected to the transmitter/receiver unit wherein the switch can activate the transmitter/receiver unit when an activation signal is received from the activation switch; and
   b) a remote control comprising a data input unit, an activation unit for activating the activation switch of the medical device and a transmitter/receiver unit able to exchange data with the transmitter/receiver unit of the medical device;
   c) wherein the medical device is configured such that the medical device is in an idle energy state when the transmitter/receiver units are not in communication.

2. The medical system as claimed in claim 1, wherein the medical device comprises at least one of a sensor, a glucose sensor, an infusion system, a pump, an insulin pump or an injection pen.

3. The medical system as claimed in claim 1, wherein the remote control comprises a glucose measuring device.

4. The medical system as claimed in claim 1, wherein the activation switch comprises at least one of an induction coil, a magnetic switch, a reed contact, a microphone, a light-sensitive switch, a photo-diode or a mechanical switch.

5. The medical system as claimed in claim 1, wherein the activation unit comprises at least one of an induction coil and a permanent magnet.

6. The medical system as claimed in claim 1, wherein the remote control comprises a data output unit.

7. The medical system as claimed in claim 1, wherein the remote control comprises an interface for communicating with at least one of an electronic device, a PC, a mobile telephone or PDA.

8. A method of using a medical system comprising the steps of:

providing a medical device comprising a communication unit and an activation element connected to the communication unit wherein the activation element activates the communication unit and wherein the medical device is in an idle energy state;

providing a remote control comprising a data input unit, an activation unit for activating the activation element of the medical appliance and a communication unit able to communicate with the communication unit of the medical appliance;

placing the medical device and remote control in proximity sufficient for the communication units to initiate communicate with each other; and activating, by the remote control, the medical device from the idle energy state prior to communication between the communication units.

9. The method of claim 8, wherein after the communication is initiated, the activation element remains activated for a predefined period which substantially corresponds to an amount of time necessary to transmit a predefined amount of data.

10. A medical system comprising:
a) a medical device configured to be carried on a user's skin, comprising a transmitter/receiver unit and an activation switch connected to the transmitter/receiver unit wherein the switch can activate the transmitter/receiver unit when an activation signal is received from the activation switch;
b) a remote control comprising a data input unit, a display unit, and an activation unit for activating the activation switch of the medical device and a transmitter/receiver unit able to exchange data with the transmitter/receiver unit of the medical device;
c) wherein the data input unit is configured for entering control signals which are transmittable to the medical device for controlling an operating mode of the medical device;
d) wherein the display unit is configured for displaying information relating to operation of the medical device; and
e) wherein the medical device is configured such that the medical device is in an idle energy state when the transmitter/receiver units are not in communication.

11. The medical system as claimed in claim 10, wherein the medical device is an infusion pump and the remote control is a blood sugar measuring device.

* * * * *

UNITED STATES PATENT AND TRADEMARK OFFICE
CERTIFICATE OF CORRECTION

PATENT NO. : 7,782,192 B2  Page 1 of 1
APPLICATION NO. : 11/924236
DATED : August 24, 2010
INVENTOR(S) : Joel Jeckelmann et al.

It is certified that error appears in the above-identified patent and that said Letters Patent is hereby corrected as shown below:

| Column | Line | PTO | Should Read |
|---|---|---|---|
| Title Page | (75) Inventors | "Michael Shoemaker" | --Michael Schoemaker-- |
| Title Page | (75) Inventors | "Sybille Fankhauser" | --Sybille Frankhauser-- |
| 10 | 10 | activation switch; | --activation switch; and-- |

Signed and Sealed this

Sixteenth Day of November, 2010

David J. Kappos
*Director of the United States Patent and Trademark Office*